United States Patent [19]

Heinemann et al.

[11] Patent Number: 5,036,085
[45] Date of Patent: Jul. 30, 1991

[54] PESTICIDAL THIADIAZOLE-SUBSTITUTED ACRYLIC ACID ESTERS AND INTERMEDIATES THEREFOR

[75] Inventors: Ulrich Heinemann, Leichlingen; Gerd Kleefeld; Stefan Dutzmann, both of Duesseldorf; Gerd Hänssler, Leverkusen, all of Fed. Rep. of Germany

[73] Assignee: Bayer Aktiengesellschaft, Leverkusen, Fed. Rep. of Germany

[21] Appl. No.: 495,528

[22] Filed: Mar. 19, 1990

[30] Foreign Application Priority Data

Mar. 31, 1989 [DE] Fed. Rep. of Germany ....... 3910358

[51] Int. Cl.$^5$ .................... C07D 285/08; A61K 31/41
[52] U.S. Cl. .................................... 514/361; 548/128; 548/129
[58] Field of Search ................ 548/128, 124; 514/361

[56] References Cited

FOREIGN PATENT DOCUMENTS

| | | | |
|---|---|---|---|
| 2037474 | 4/1971 | Fed. Rep. of Germany | 514/361 |
| 2635568 | 2/1977 | Fed. Rep. of Germany | 514/361 |
| 3228131 | 2/1984 | Fed. Rep. of Germany | 514/361 |

*Primary Examiner*—Robert Gerstl
*Attorney, Agent, or Firm*—Sprung, Horn, Kramer & Woods

[57] ABSTRACT

Fungicidal thiadiazole-substituted acrylic acid esters of the formula

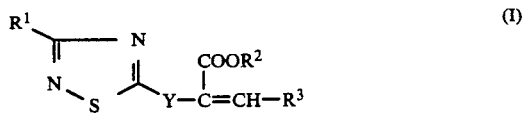

(I)

in which $R^1$ represents hydrogen, unsubstituted or substituted alkyl or alkenyl, or in each case unsubstituted or substituted aralkyl, aralkenyl, aryl or heteroaryl,
$R^2$ represents alkyl,
$R^3$ represents dialkyl amino or a radical $-Z-R^4$,
Y represents oxygen, sulphur or a radical

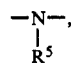

$R^4$ represents alkyl or unsubstituted or substituted aralkyl,
$R^5$ represents hydrogen or alkyl and
Z represents oxygen or sulphur.

13 Claims, No Drawings

PESTICIDAL THIADIAZOLE-SUBSTITUTED ACRYLIC ACID ESTERS AND INTERMEDIATES THEREFOR

The invention relates to novel thiadiazole-substituted acrylic acid esters, to a number of processes for their preparation, to their use for combating pests and to new intermediates.

It is known that certain substituted acrylic acid esters such as, for example, the compound methyl 3-methoxy-2-(2-methylphenyl)-acrylate possess fungicidal properties (compare, for example, EP 178,826).

However, the activity of these previously known compounds is not completely satisfactory in all application areas, in particular at low application rates and concentrations.

New thiadiazole-substituted acrylic acid esters of the general formula (I)

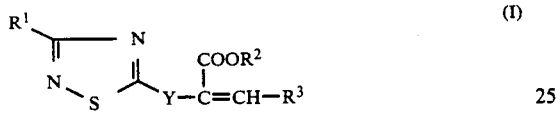

in which
- $R^1$ represents hydrogen, unsubstituted or substituted alkyl or alkenyl, or in each case unsubstituted or substituted aralkyl, aralkenyl, aryl or heteroaryl,
- $R^2$ represents alkyl,
- $R^3$ represents dialkylamino or a radical $-Z-R^4$,
- Y represents oxygen, sulphur or a radical

- $R^4$ represents alkyl or unsubstituted or substituted aralkyl,
- $R^5$ represents hydrogen or alkyl and
- Z represents oxygen or sulphur, have been found.

The compounds of the formula (I) can exist as geometric isomers or isomer mixtures of different composition. Both the pure isomers and the isomer mixtures are according to the invention.

It has furthermore been found that the new thiadiazole-substituted acrylic acid esters of the general formula (I)

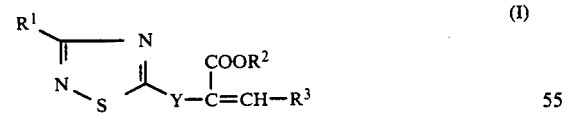

in which
- $R^1$ represents hydrogen, unsubstituted or substituted alkyl or alkenyl, or in each case unsubstituted or substituted aralkyl, aralkenyl, aryl or heteroaryl,
- $R^2$ represents alkyl,
- $R^3$ represents dialkylamino or a radical $-Z-R^4$,
- Y represents oxygen, sulphur or a radical

- $R^4$ represents alkyl or unsubstituted or substituted aralkyl,
- $R^5$ represents hydrogen or alkyl and
- Z represents oxygen or sulphur, are obtained by one of the following processes:

(a) Thiadiazole-substituted acrylic acid esters of the formula (Ia)

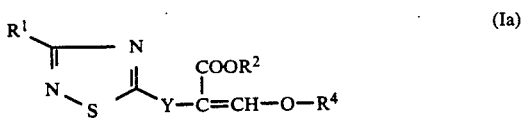

in which
$R^1$, $R^2$, $R^4$ and Y have the abovementioned meanings, are obtained when hydroxyacrylic acid esters or their alkali metal salts of the formula (II)

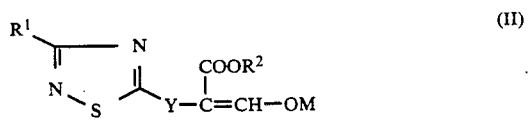

in which
M represents hydrogen or an alkali metal cation and
$R^1$, $R^2$ and Y have the abovementioned meanings
are reacted with alkylating agents of the formula (III)

in which
$E^1$ represents an electron-withdrawing leaving group and
$R^4$ has the abovementioned meaning,
if appropriate in the presence of a diluent and if appropriate in the presence of a reaction auxiliary, or (b) thiadiazole-substituted acrylic acid esters of the formula (Ib)

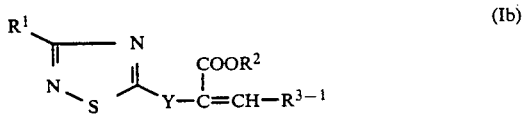

in which
$R^{3-1}$ represents dialkylamino and
$R^1$, $R^2$ and Y have the abovementioned meanings,
are obtained when substituted acetic acid esters of the formula (IV)

in which
$R^1$, $R^2$ and Y have the abovementioned meanings,
are reacted with formamide of the formula (V)

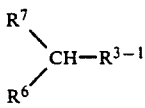

in which
R$^6$ and R$^7$ independently of one another in each case represent alkoxy or dialkylamino and
R$^{3\text{-}1}$ has the abovementioned meaning,
if appropriate in the presence of a diluent; or
(c) thiadiazole-substituted acrylic acid esters of the formula (Ic)

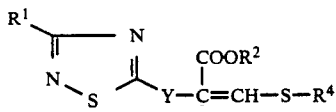

in which
R$^1$, R$^2$, R$^4$ and Y have the abovementioned meanings, are obtained when substituted acrylic acid esters of the formula (VI)

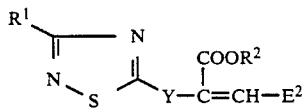

in which
E$^2$ represents an electron-attracting leaving group and
R$^1$, R$^2$ and Y have the abovementioned meanings, are reacted with thiols of the formula (VII)

$$R^4\text{—SH} \qquad (VII)$$

in which
R$^4$ has the abovementioned meaning,
if appropriate in the presence of a diluent and if appropriate in the presence of a reaction aid.

Finally, it has been found that the new thiadiazole-substituted acrylic acid esters of the general formula (I) possess a good action against pests.

Surprisingly, the thiadiazole-substituted acrylic acid esters of the general formula (I) according to the invention show, for example, a considerably better fungicidal activity than the acrylic acid esters known from the prior art, such as, for example, the compound methyl 3-methoxy-2-(2-methylphenyl)-acrylate, which are closely related compounds chemically and with respect to their action.

Preferred substituents or ranges of the radicals shown in the formulae mentioned above and below are illustrated in the following:

Unsubstituted or substituted alkyl in the definitions of R$^1$, R$^2$, R$^4$ and R$^5$ in the general formulae is represented by straight-chain or branched alkyl preferably having 1 to 10, particularly preferably 1 to 8 and in particular 1 to 4, carbon atoms. Examples which may be mentioned are unsubstituted or substituted methyl, ethyl, n-propyl, i-propyl, n-butyl, sec-butyl, i-butyl, t-butyl, n-pentyl, i-pentyl and t-pentyl.

The term unsubstituted or substituted alkenyl in the definitions of R$^1$ in the general formulae is represented by straight-chain or branched alkenyl preferably having 2 to 8, particularly preferably 2 to 6 and in particular 2 to 4, very particularly preferably 3 carbon atoms. Examples which may be mentioned are unsubstituted or substituted vinyl, allyl, prop-2-enyl, but-1-enyl, but-2-enyl, but-3-enyl and 1-methylallyl.

Dialkylamino in the definition of R$^3$ represents an amino group having two alkyl groups, which in each case can be straight-chain or branched, or identical or different and preferably in each case contain 1 to 6, in particular 1 to 4 carbon atoms, where methyl, ethyl, n- and i-propyl may be mentioned. Examples which may be mentioned are dimethylamino, diethylamino, di-n-propylamino and di-i-propylamino.

The term unsubstituted or substituted aryl in the definition of R$^1$ in the general formulae is taken as meaning aryl preferably having 6 to 10 carbon atoms in the aryl moiety. Examples which may be mentioned are unsubstituted or substituted phenyl or naphthyl, in particular phenyl.

Unsubstituted or substituted aralkyl in the definitions of R$^1$ and R$^4$ preferably contain 1 to 6 carbon atoms in the straight-chain or branched alkyl moiety and preferably phenyl as the aryl moiety. Examples of aralkyl groups which may be mentioned are benzyl and phenethyl.

Unsubstituted or substituted aralkenyl in the definition of R$^1$ preferably contains 2 to 6, in particular 2 to 4, very particularly preferably 3 carbon atoms in the straight-chain or branched alkenyl moiety and preferably phenyl as the aryl moiety. An example of an aralkenyl group which may be mentioned is styryl.

Heteroaryl in the definition of R$^1$ in general represents a 5- or 6-membered ring which contains one or more heteroatoms, preferably 1 to 3 identical or different heteroatoms. Oxygen, sulphur and nitrogen may be preferably mentioned as heteroatoms; examples which may be mentioned are; pyridyl, thienyl or furyl.

The substituents for the aryl radicals as such or in combinations such as arylalkyl, aryloxy, arylthio, aralkyloxy and for the heterocyclic rings such as heteroarylalkyl and heteroaryl especially have the following meanings.

Halogen as a substituent of the radicals in general represents fluorine, chlorine, bromine and iodine, preferably fluorine, chlorine and bromine, particularly preferably fluorine and chlorine.

Alkyl as a substituent of the radicals alone or in combinations such as alkoximinoalkyl in general represents straight-chain or branched alkyl, preferably having 1 to 6, particularly preferably having 1 to 4 carbon atoms, methyl, ethyl and t-butyl being very particularly preferred. The enumeration of examples corresponds to that given above.

Alkoxy as a substituent of the radicals alone or in combinations such as alkoximinoalkyl in general represents straight-chain or branched alkoxy having 1 to 6, particularly preferably 1 to 3 carbon atoms per alkyl radical; examples which may be mentioned are: methoxy, ethoxy, n- and i-propoxy, n-, i-, s- and t-butoxy, n-hexoxy and i-hexoxy.

Alktlthio as a substituent in the radicals in general represents straight-chain or branched alkylthio preferably having 1 to 6 carbon atoms, for example the following groups are to be understood hereunder: methylthio, ethylthio, propylthio, butylthio, pentylthio and their isomers, such as, for example, i-propylthio, i-, s- and t-butylthio, 1-methyl-butylthio, 2-methyl-butylthio and 3-methyl-butylthio. Preferred alkylthio radicals contain 1 to 4 carbon atoms. Methylthio, ethylthio, n-, i- and s-propylthio and n-, i-, s- and t-butylthio are particularly preferred.

Halogenoalkyl and halogenoalkoxy as substituents in the radicals in general represent straight-chain or branched radicals each having 1 to 4 carbon atoms, particularly preferably having 1 or 2 carbon atoms and in each case 1 to 9, or respectively 1 to 5, identical or different halogen atoms such as defined under halogen; examples which may be mentioned are: fluoromethyl, chloromethyl, bromomethyl, fluoroethyl, chloroethyl, bromoethyl, fluoro-n-propyl, chloro-n-propyl, difluoromethyl, trifluoromethyl, dichloromethyl, trichloromethyl, difluoroethyl, trifluoroethyl, trichloroethyl, chlorodifluoro-methyl, trifluoro-chloroethyl, chlorobutyl, fluorobutyl, fluoromethoxy, chloromethoxy, bromomethoxy, fluoroethoxy, chloroethoxy, bromoethoxy, fluoropropoxy, chloropropoxy, bromopropoxy, fluorobutoxy, chlorobutoxy, fluoro-i-propoxy, chloro-i-propoxy, difluoromethoxy, trifluoromethoxy, dichloromethoxy, trichloromethoxy, difluoroethoxy, trifluoroethoxy, tetrafluoroethoxy, trichloroethoxy, chlorodifluoromethoxy and trifluorochloroethoxy.

Halogenoalkylthio as a substituent in the radicals in general represents straight-chain or branched radicals each having 1 to 4 carbon atoms, particularly preferably having 1 or 2 carbon atoms and in each case 1 to 9, or respectively 1 to 5, identical or different halogen atoms as defined under halogen; examples which may be mentioned are: fluoromethylthio, chloromethylthio, bromomethylthio, fluoroethylthio, chloroethylthio, bromoethylthio, fluoropropylthio, chloropropylthio, bromopropylthio, fluorobutylthio, chlorobutylthio, bromobutylthio, fluoro-i-propylthio, chloro-i-propylthio, difluoromethylthio, trifluoromethylthio, dichloromethylthio, trichloromethylthio, difluoroethylthio, trifluoroethylthio, tetrafluoroethylthio, trichloroethylthio, chlorodifluoromethylthio and trifluorochloroethylthio.

Alkoxycarbonyl as a substituent in the radicals in general represents straight-chain or branched alkoxycarbonyl having 1 to 4, preferably 1 or 2 carbon atoms in the alkoxy radical; examples which may be mentioned are: methoxycarbonyl, ethoxycarbonyl, n-propoxycarbonyl, i-propoxycarbonyl, and n-, i-, s- and t-butoxycarbonyl.

Cycloalkyl as a substituent in the radicals in general represents cycloalkyl preferably having 3 to 8, in particular 3, 5 or 6 carbon atoms. Examples which may be mentioned are unsubstituted or substituted cyclopropyl, cyclobutyl, cyclopentyl, cyclohexyl and cycloheptyl.

Formula (I) provides a general definition of the thiadiazole-substituted acrylic acid esters according to the invention. Preferred compounds of the formula (I) are those in which $R^1$ represents hydrogen, or straight-chain or branched alkyl having 1 to 8 carbon atoms which is unsubstituted or monosubstituted to polysubstituted by identical or different substituents, suitable substituents being the following:
fluorine, chlorine, bromine, iodine, or arylthio and aryloxy each having 6 to 10 carbon atoms in the aryl moiety, and in each case unsubstituted or monosubstituted to pentasubstituted by identical or different substituents, where the aryl substituents mentioned below in the definition of $R^1$ may be mentioned as aryl substituents;

$R^1$ furthermore represents straight-chain or branched alkenyl having 2 to 8 carbon atoms, aralkyl having 1 to 6 carbon atoms in the straight-chain or branched alkyl moiety, in each case unsubstituted or monosubstituted to polysubstituted in the aryl moiety by identical or different substituents, aralkenyl having 2 to 6 carbon atoms in the straight-chain or branched alkenyl moiety or aryl having 6 to 10 carbon atoms in the respective aryl moiety, suitable aryl substituents in each case being:
halogen, cyano, nitro, in each case straight-chain or branched alkyl, alkoxy or alkylthio each having 1 to 6 carbon atoms in each case straight-chain or branched halogenoalkyl, halogenoalkoxy or halogenoalkylthio each having 1 to 4 carbon atoms and 1 to 9 identical or different halogen atoms, straight-chain or branched alkoxycarbonyl having 1 to 4 carbon atoms or alkoxyiminoalkyl each having 1 to 6 carbon atoms in the individual alkyl moieties, cycloalkyl having 3 to 8 carbon atoms, doubly linked alkanediyl having 3 to 5 carbon atoms, aryl, aralkyl, aryloxy or aralkyloxy each having 6 to 10 carbon atoms in the aryl moiety and optionally 1 to 4 carbon atoms in the straight-chain or branched alkyl moiety and in each case unsubstituted or monosubstituted to polysubstituted in the aryl moiety by identical or different substituents from the series comprising halogen, alkyl, alkoxy, alkylthio, halogenoalkyl, halogenoalkoxy or halogenoalkylthio each having 1 to 4 carbon atoms and optionally 1 to 9 identical or different halogen atoms, or heteroarylalkyl or heteroaryl each having 2 to 8 carbon atoms and 1 to 4 identical or different heteroatoms, in particular nitrogen, oxygen and/or sulphur, in the heteroaryl moiety and optionally 1 to 4 carbon atoms in the straight-chain or branched alkyl moiety and in each case optionally monosubstituted to polysubstituted in the heteroaryl moiety by identical or different substituents from the series comprising halogen, alkyl, alkoxy, alkylthio, halogenoalkyl, halogenoalkoxy or halogenoalkylthio each having 1 to 4 carbon atoms and optionally 1 to 9 identical or different halogen atoms;

$R^1$ additionally represents a 5- or 6-membered heteroaryl radical having 1 to 3 identical or different heteroatoms—in particular nitrogen, oxygen and/or sulphur—and optionally monosubstituted to polysubstituted by identical or different substituents, suitable substituents being the abovementioned aryl substituents, $R^2$ represents straight-chain or branched alkyl having 1 to 6 carbon atoms, $R^3$ represents dialkylamino each having 1 to 6 carbon atoms in the individual straight-chain or branched, identical or different alkyl moieties or represents a radical $$-Z-R^4,$$

Y represents oxygen, sulphur or a radical $$-\underset{R^5}{N}-,$$

$R^4$ represents straight-chain or bran alkyl having 1 to 6 carbon atoms or aralkyl having 1 to 4 carbon atoms in the straight-chain or branched alkyl moiety and 6 to 10 carbon atoms in the aryl moiety and unsubstituted or monosubstituted to polysubstituted in the aryl moiety by identical or different substituents, suitable aryl substituents being those mentioned for R¹, R⁵ represents hydrogen or straight-chain or branched alkyl having 1 to 6 carbon atoms and Z represents oxygen or sulphur.

Particularly preferred compounds of the formula (I) are those in which

R¹ represents hydrogen, methyl, ethyl, n- or i-propyl, n-, i-, s- or t-butyl, straight-chain or branched alkyl having 1 to 4 carbon atoms, which is monosubstituted to hexasubstituted by identical or different substituents from the series comprising fluorine and chlorine, or straight-chain or branched alkyl having 1 to 4 carbon atoms which is substituted by phenylthio or phenyloxy which in each case are unsubstituted or monosubstituted to trisubstituted by identical or different substituents, suitable phenyl substituents which may be mentioned being the substituents mentioned below in the definition of R¹;

R¹ represents allyl, n- or i-butenyl, or benzyl, phenylethyl, phenylethenyl, phenyl, naphthyl, pyridyl, thienyl or furyl in each case optionally monosubstituted to trisubstituted in the aryl moiety or in the heteroaryl moiety by identical or different substituents, suitable substituents in each case being:

fluorine, chlorine, bromine, cyano, nitro, methyl, ethyl, n- or i-propyl, n-, i-, s- or t-butyl, methoxy, ethoxy, n- or i-propoxy, methylthio, trifluoromethyl, trifluoromethoxy, difluoromethoxy, trifluoromethylthio, methoxycarbonyl, ethoxycarbonyl, methoximinomethyl, ethoximinomethyl, methoximinoethyl, ethoximinoethyl, cyclopentyl, cyclohexyl, 1,3-propanediyl, but-2-ene-di-1,4-yl, 1,4-butanediyl, or phenyl, benzyl, phenoxy or benzyloxy in each case unsubstituted or monosubstituted to different substituents from the series comprising fluorine, chlorine, bromine, methyl, ethyl, methoxy, ethoxy, methylthio, trifluoromethyl, difluoromethoxy, trifluoromethoxy and trifluoromethylthio, R² represents methyl, ethyl, n- or i-propyl, n-, i-, s- or t-butyl, R³ represents dialkylamino each having 1 to 4 carbon atoms in the individual straight-chain or branched, identical or different alkyl moieties or a radical —Z—R⁴, Y represents oxygen, sulphur or a radical

R⁴ represents methyl, ethyl, n- or i-propyl, n-, i-, s- or t-butyl or benzyl which is unsubstituted or monosubstituted to trisubstituted by identical or different substituents, suitable substituents being those mentioned for R¹;

R⁵ represents hydrogen, methyl, ethyl, n- or i-propyl, n-, i-, s- or t-butyl and Z represents oxygen or sulphur.

Very particularly preferred compounds of the formula (I) are those in which

R¹ represents hydrogen, methyl, ethyl, n- or i-propyl, t-butyl, alkyl having 1 or 2 carbon atoms, which is monosubstituted to pentasubstituted by identical or different substituents from the series comprising fluorine and chlorine or alkyl having 1 or 2 carbon atoms, which is substituted by phenylthio and phenyloxy which are in each case unsubstituted or monosubstituted or disubstituted by identical or different substituents, suitable phenyl substituents which may be mentioned being those mentioned below in the definition of R¹ or R¹ represents phenyl or naphthyl in each case optionally monosubstituted to trisubstituted by identical or different substituents, suitable substituents in each case being: fluorine, chlorine, bromine, cyano, nitro, methyl, ethyl, n- or i-propyl, n-, i-, s- or t-butyl, methoxy, ethoxy, n- or i-propoxy, methylthio, trifluoromethyl, trifluoromethoxy, difluoromethoxy, trifluoromethylthio, methoxycarbonyl, ethoxycarbonyl, methoximinomethyl, ethoximinomethyl, methoximinoethyl, ethoximinoethyl, cyclopentyl, cyclohexyl, 1,3-propanediyl, 1,4-butanediyl or phenyl, phenoxy, benzyl or benzyloxy in each case optionally monosubstituted or disubstituted by identical or different substituents from the series comprising fluorine, chlorine, bromine, methyl and ethyl, R² represents methyl or ethyl R³ represents dimethylamino, diethylamino or a radical —Z—R⁴, Y represents oxygen, sulphur or a radical

R⁴ represents methyl, ethyl, n- or i-propyl or benzyl,

R⁵ represents hydrogen, methyl or ethyl and

Z represents oxygen or sulphur.

Especially preferred compounds of the formula (I) are those in which

R¹ represents hydrogen, methyl, ethyl, n- or i-propyl, t-butyl, methyl which is monosubstituted to trisubstituted by identical or different substituents from the series comprising fluorine and chlorine or phenyl, phenyloxymethyl or phenylthiomethyl which are in each case optionally monosubstituted or disubstituted by identical or different substituents, suitable substituents being:

fluorine, chlorine, bromine, cyano, nitro, methyl, ethyl, methoxy, ethoxy, methylthio, trifluoromethyl, trifluoromethoxy, trifluoromethylthio, methoxycarbonyl, ethoxycarbonyl, methoximinomethyl, cyclopentyl, 1,3-propanediyl, methoximinoethyl or phenyl, phenoxy, benzyl or benzyloxy which are optionally monosubstituted or disubstituted by identical or different substituents from the series comprising fluorine, chlorine, bromine or methyl, R² represents methyl or ethyl, R³ represents methoxy, ethoxy, methylthio or dimethylamino and Y represents an N-methyl radical or sulphur.

In addition to the compounds mentioned in the preparation examples, the thiadiazole-substituted acrylic acid esters of the general formula (I)

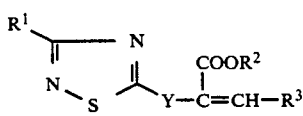

shown in the following Table 1 may be mentioned in particular:

TABLE 1

| R¹ | R² | R³ | Y |
|---|---|---|---|
| ![pyridyl] | CH₃ | OCH₃ | N—CH₃ |
| ![benzyl, CH₂—] | CH₃ | OCH₃ | N—CH₃ |
| ![styryl, CH=CH—] | CH₃ | OCH₃ | N—CH₃ |
| ![phenylthiomethyl, S—CH₂—] | CH₃ | OCH₃ | N—CH₃ |

If, for example, methyl N-(3-phenyl-1,2,4-thiadiazol-5-yl)-N-methyl-2-amino-3-hydroxy-acrylate and dimethyl sulphate are used as starting substances, the course of the reaction of process (a) according to the invention can be represented by the following equation:

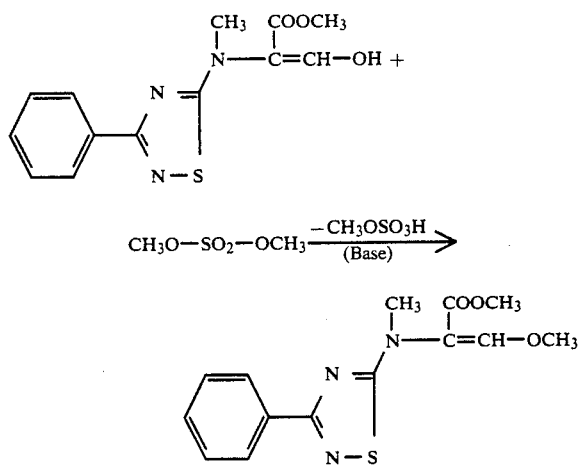

If, for example, N-(3-trifluoromethyl-1,2,4-thiadiazol-5-yl)-N-methyl-glycine methyl ester and dimethylformamide dimethyl acetal are used as starting substances, the course of the reaction of process (b) according to the invention can be represented by the following equation:

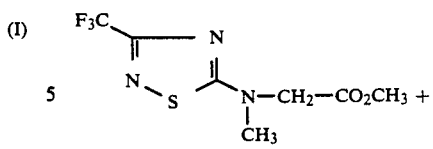

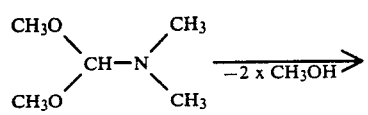

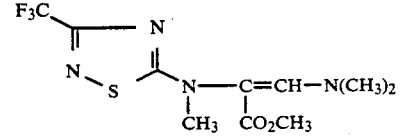

If, for example, methyl N-(3-phenyl-1,2,4-thiadiazol-5-yl)-N-methyl-2-amino-3-methylsulphonyloxy-acrylate and methylmercaptan are used as starting substances, the course of the reaction of process (c) according to the invention can be represented by the following equation:

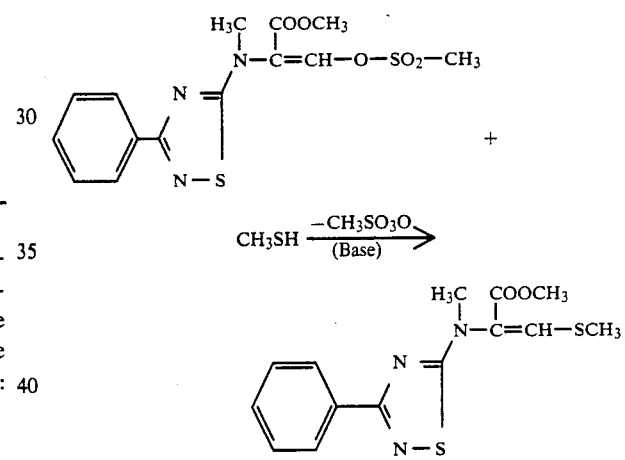

Formula (II) provides a general definition of the hydroxyacrylic acid esters or their alkali metal salts required as starting substances for carrying out process (a) according to the invention. In this formula (II), R¹, R² and Y preferably represent those radicals which have already been mentioned as preferred for these substituents in connection with the description of the substances of the formula (I) according to the invention.

M preferably represents hydrogen or a sodium, potassium or lithium cation.

The hydroxyacrylic acid esters of the formula (II) are hitherto unknown and also a subject of the invention.

They are obtained when substituted acetic acid esters of the formula (IV)

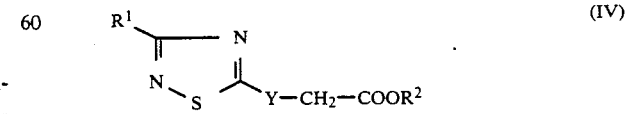

in which
R¹, R² and Y have the abovementioned meanings, are reacted with formic acid esters of the formula (VIII)

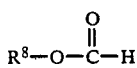

(VIII)

in which
R[8] represents alkyl in particular methyl or ethyl
if appropriate in the presence of a diluent, such as, for example, dimethylformamide, and if appropriate in the presence of a basic reaction aid, such as, for example, sodium hydride, at temperatures between −20° C. and +50° C., and if appropriate are then hydrolyzed with an acid, such as, for example, hydrochloric acid.

Formic acid esters of the formula (VIII) are generally known compounds of organic chemistry.

Formula (III) provides a general definition of the alkylating agents furthermore required as starting substances for carrying out process (a) according to the invention. In this formula (III), R[4] preferably represents those radicals which have already been mentioned as preferred for this substituent in connection with the description of the substances of the formula (I) according to the invention.

E[1] represents a customary leaving group in alkylating agents, preferably an optionally substituted alkyl, alkoxy or arylsulphonyloxy radical, such as, for example, a methoxysulphonyloxy radical, an ethoxysulphonyloxy radical or a p-toluenesulphonyloxy radical or halogen, in particular chlorine, bromine or iodine.

The alkylating agents of the formula (III) are generally known compounds of organic chemistry.

Formula (IV) provides a general definition of the substituted acetic acid esters required as starting substances for carrying out process (b) according to the invention and for the synthesis of the precursors of the formula (II). In this formula (IV), R[1], R[2] and Y preferably represent those radicals which have already been mentioned as preferred for these substituents in connection with the description of the substances of the formula (I) according to the invention.

Some of the substituted acetic acid esters of the formula (IV) are known (compare, for example, U.S. Pat. No. 4,207,090, GB 1,574,430, DE 2,050,346 and Yakugaku Zasshi, 88, 1437-49 [1968]).

Substituted acetic acid esters of the formula (IVa)

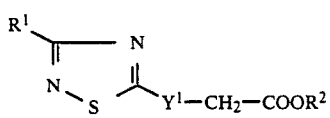

(IVa)

in which
Y[1] represents oxygen or an N-alkyl radical, preferably having 1 to 4 carbon atoms, in particular an N-methyl radical or an N-ethyl radical and
R[1] and R[2] have the abovementioned meanings, excluding the compounds N-methyl-N-[3-(trichloromethyl)-1,2,4-thiadiazol-5-yl]-glycine ethyl ester and N-methyl-N-[3-(trifluoromethyl)-1,2,4-thiadiazol-5-yl]-glycine ethyl ester (compare U.S. Pat. No. 4,207,090),
are hitherto unknown and also a subject of the invention.

The new substituted acetic acid esters of the formula (IVa) are obtained by reacting 1,2,4-thiadiazole derivatives of the formula (IX)

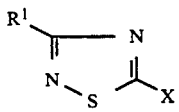

(IX)

in which
R[1] has the abovementioned meaning and
X represents halogen, preferably fluorine or chlorine, in particular chlorine,
with acetic acid ester derivatives of the formula (X)

$$HY^1-CH_2-COOR^2 \qquad (X)$$

in which
R[2] and Y[1] have the abovementioned meanings, or their hydrochlorides,
if appropriate in the presence of a diluent and if appropriate in the presence of a base.

The process for the preparation of the new substituted acetic acid esters of the formula (IVa) according to the invention is preferably carried out using diluents. Those which are suitable are inert organic solvents. These particularly include aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform or carbon tetrachloride, ethers, such as diethyl ether, dioxane, tetrahydrofuran or ethylene glycol dimethyl ether or ethylene glycol diethyl ether, nitriles, such as acetonitrile or propionitrile, amides, such as dimethylformamide, dimethylacetamide, N-methylformanilide, N-methylpyrrolidone or hexamethylphosphoramide or sulphoxides, such as dimethyl sulphoxide.

The process according to the invention for the preparation of the new starting compounds is preferably carried out in the presence of a suitable basic reaction auxiliary. Those which are suitable are preferably all customarily utilizable inorganic and organic bases. Hydrides, hydroxides, amides, alkoxides, carbonates or hydrogencarbonates of alkali metals, such as, for example, sodium hydride, sodium amide, sodium hydroxide, sodium methoxide, sodium ethoxide, potassium t-butoxide, sodium carbonate or sodium hydrocarbonate or else tertiary amines, such as, for example, triethylamine, N,N-dimethylaniline, pyridine, N,N-dimethylaminopyridine, diazabicyclooctane (DABCO), diazabicyclononene (DBN) or diazabicycloundecene (DBU) are preferably used.

The reaction temperatures can be varied within a relatively wide range when carrying out process (a) according to the invention. In general, the reaction is carried out at temperatures between −50° C. and +200° C., preferably at temperatures between −20° C. and +150° C.

In order to carry out the process according to the invention, the starting components and the bases are generally employed in an equivalent ratio. An excess of one component or the other usually has no substantial advantages. The reaction components are in general combined in one of the abovementioned solvents in the presence of the base and stirred for one or more hours at the corresponding temperature. The working up of the reaction mixture is carried out by customary methods.

The thiadiazole derivatives of the formula (IX) are known or can be obtained in analogy to known processes (compare, for example, DE 2,242,185, DE 3,228,147, Chem. Ber. 90, 182 [1957] ibid. 892 [1957]).

The acetic acid ester derivatives of the formula (X) are generally known compounds of organic chemistry.

Formula (V) provides a general definition of the formamide derivatives furthermore required as starting substances for carrying out process (b) according to the invention. In this formula $R^{3-1}$ preferably represents dialkylamino having 1 to 6, in particular having 1 to 4 carbon atoms in the individual straight-chain or branched alkyl moieties. $R^{3-1}$ very particularly preferably represents dimethylamino or diethylamino.

$R^6$ and $R^7$ preferably independently of one another in each case represent straight-chain or branched alkoxy having 1 to 4 carbon atoms, in particular methoxy or ethoxy, or a dialkylamino radical in each case having 1 to 6, in particular 1 to 4 carbon atoms, in the individual straight-chain or branched alkyl moieties.

The formamide derivatives of the formula (V) are generally known compounds of organic chemistry.

Formula (VI) provides a general definition of the substituted acrylic acid esters required as starting substances for carrying out process (c) according to the invention. In this formula (VI), $R^1$, $R^2$ and Y preferably represent those radicals which have already been mentioned as preferred for these substituents in connection with the description of the substances of the formula (I) according to the invention.

$E^2$ preferably represents a suitable acyloxy or sulphonyloxy radical, in particular an acetoxy, a methanesulphonyloxy or a p-toluenesulphonyloxy radical.

The substituted acrylic acid esters of the formula (VI) are hitherto unknown.

They are obtained when hydroxyacrylic acid esters of the formula (II)

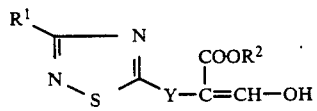

(II)

in which
  $R^1$, $R^2$ and Y have the abovementioned meanings,
are reacted with acid chlorides of the formula (XI)

—Cl    (XI)

in which
  $R^9$ represents an acyl or sulphonyl radical, in particular an acetyl, a methanesulphonyl or a p-toluenesulphonyl radical,
if appropriate in the presence of a diluent, such as, for example, dichloromethane, and if appropriate in the presence of an acid-binding agent, such as, for example, triethylamine or pyridine, at temperatures between $-20°$ C. and $+120°$ C.

Acid chlorides of the formula (XI) are generally known compounds of organic chemistry.

Formula (VII) provides a general definition of thiols furthermore required as starting substances for carrying out process (c) according to the invention. In this formula (VII), $R^4$ preferably represents those radicals which have already been mentioned as preferred for this substituent in connection with the description of the substances of the formula (I) according to the invention.

The thiols of the formula (VII) are generally known compounds of organic chemistry.

Suitable diluents for carrying out process (a) according to the invention are inert organic solvents. These particularly include aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform or carbon tetrachloride, ethers, such as diethyl ether, dioxane, tetrahydrofuran or ethylene glycol dimethyl ether or ethylene glycol diethyl ether, nitriles, such as acetonitrile or propionitrile, amides, such as dimethylformamide, dimethylacetamide, N-methylformanilide, N-methylpyrrolidone or hexamethylphosphoramide or sulphoxides, such as dimethyl sulphoxide.

Process (a) according to the invention can optionally also be carried out in two-phase systems, such as, for example, water/toluene or water/dichloromethane, if appropriate in the presence of a phase transfer catalyst. Examples of such catalysts which may be mentioned are: tetrabutylammonium iodide, tetrabutylammonium bromide, tributyl-methylphosphonium bromide, trimethyl-$C_{13}/C_{15}$-alkylammonium chloride, dibenzyldimethyl-ammonium methylsulphate, dimethyl-$C_{12}/C_{14}$-alkylbenzylammonium chloride, tetrabutylammonium hydroxide, 15-crown-5, 18-crown-6, triethylbenzylammonium chloride, trimethylbenzylammonium chloride or tris-[2-(2-methoxyethoxy)-ethyl]-amine.

Process (a) according to the invention is preferably carried out in the presence of a suitable basic reaction auxiliary. Those which are suitable are all customarily utilizable inorganic and organic bases. Hydrides, hydroxides, amides, alkoxides, carbonates or hydrogencarbonates of alkali metals, such as, for example, sodium hydride, sodium amide, sodium hydroxide, sodium methoxide, sodium ethoxide, potassium t-butoxide, sodium carbonate or sodium hydrogencarbonate or else tertiary amines, such as for example, triethylamine, N,N-dimethylaniline, pyridine, N,N-dimethylaminopyridine, diazabicyclooctane (DABCO), diazabicyclononene (DBN) or diazabicycloundecene (DBU) are preferably used.

The reaction temperatures can be varied within a relatively large range when carrying out process (a) according to the invention. In general, the reaction is carried out at temperatures between $-30°$ C. and $+120°$ C., preferably at temperatures between $-20°$ C. and $+60°$ C.

In order to carry out process (a) according to the invention, 1.0 to 10.0 moles, preferably 1.0 to 5.0 moles, of alkylating agent of the formula (III) and optionally 1.0 to 5.0 moles, preferably 1.0 to 2.0 moles, of reaction auxiliary are in general employed per mole of 3-hydroxyacrylic acid ester or a corresponding alkali metal salt of the formula (II). It is also possible here to prepare the 3-hydroxyacrylic acid esters or their alkali metal salts of the formula (II) required as starting compounds for carrying out process (a) according to the invention directly in the reaction vessel in a preliminary reaction and to react further directly from the reaction mixture without isolation with the alkylating agent of the formula (III) in accordance with process (a) according to the invention ("one-pot process"). The reaction is carried out, and the reaction products are worked up and isolated by generally customary methods (also compare the preparation examples).

Suitable diluents for carrying out process (b) according to the invention are inert organic solvents. These particularly include aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform, carbon tetrachloride or ethers, such as diethyl ether, dioxane, tetrahydrofuran or ethylene glycol dimethyl ether or ethylene glycol diethyl ether.

However, it is also possible to carry out process (b) according to the invention without addition of a diluent.

The reaction temperatures can be varied within a relatively wide range when carrying out process (b) according to the invention. In general, the reaction is carried out at temperatures between −20° C. and +220° C., preferably at temperatures between 0° C. and 200° C.

In order to carry out process (b) according to the invention, 1.0 to 30.0 moles, preferably 1.0 to 15.0 moles, of formamide-derivatives of the formula (V) are in general employed per mole of substituted acetic acid ester of the formula (IV). The reaction is carried out, and the reaction products are worked up and isolated by generally customary methods (compare also here G. Mathieu; J. Weill-Raynel "Formation of C—C Bond", Vol. I; pp. 229-244; Thieme Verlag Stuttgart 1973).

Suitable diluents for carrying out process (c) according to the invention are inert organic solvents. These particularly include aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform or carbon tetrachloride, ethers, such as diethyl ether, dioxane, tetrahydrofuran or ethylene glycol dimethyl ether or ethylene glycol diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoramide, esters, such as ethyl acetate or sulphoxides, such as dimethyl sulphoxide.

Process (c) according to the invention is preferably carried out in the presence of a suitable reaction auxiliary. Those which are suitable are all customary inorganic and organic bases. These include, for example, alkali metal hydroxides, such as sodium hydroxide or potassium hydroxide, alkali metal carbonates, such as sodium carbonate, potassium carbonate or sodium hydrogencarbonate, or tertiary amines, such as triethylamine, N,N-dimethylaniline, pyridine, N,N-dimethylaminopyridine, diazabicyclooctane (DABCO), diazabicyclononene (DBN) or diazabicycloundecene (DBU) are preferably used.

The reaction temperatures can be varied within a relatively large range when carrying out process (c) according to the invention. In general, the reaction is carried out at temperatures between −20° C. and 180° C., preferably at temperatures between 0° C. and 150° C.

The process according to the invention can also optionally be carried out under pressure, depending on the boiling point of the reaction component used, for example when using low-boil thiols of the formula (VII). Preferably, the reaction is then carried out at the pressure which is attained under the reaction conditions on heating to the required reaction temperature.

In order to carry out process (c) according to the invention, 1.0 to 20.0 moles, preferably 1.0 to 5.0 moles of thiol of the formula (VII) and optionally 1.0 to 5.0 moles, preferably 1.0 to 1.5 moles of reaction aid are in general employed per mole of substituted acrylic acid ester of the formula (VI). The reaction is carried out, and the reaction products are worked up and isolated up by generally customary methods.

The active compounds according to the invention exhibit a strong action against pests and can be employed practically for combating undesired injurious organisms. The active compounds are suitable for use, for example, as plant protection agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation:

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubensis;*

Plasmopara species, such as, for example, *Plasmopara viticola;*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: Helminthosporium);

Uromyces species, such as, for example, *Uromyces appendiculatus;*

Puccinia species, such as, for example, *Puccinia recondita;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Alternaria species, such as, for example, *Alternaria brassicae* and

Pseudocercosporella species, such as, for example, *Pseudocercosporella herpotrichoides*.

The good toleration, by plants, of the active compounds, at the concentrations required for combating plant diseases, permits treatment of above-ground parts of plants, of vegetative propagation stock and seeds, and of the soil.

The active compounds according to the invention can be employed here with particularly good effect for the protective combating of cereal diseases, such as, for example, against the causative organism of wheat leaf spot (*Leptosphaeria nodorum*) or for the protective combating of rice diseases, such as for example, against the causative organism of rotten neck of rice (*Pyricularia oryzae*).

Moreover, some of the active compounds according to the invention additionally show a fungicidal action against true mildew fungi, inter alia in cereals, and in apple scab.

Depending on their particular physical and/or chemical properties, the active compounds can be converted to the customary formulations, such as solutions, emulsions, suspensions, powders, foams, pastes, granules, aerosols, very fine capsules in polymeric substances and in coating compositions for seed, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant those liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, aluminas, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural minerals such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, and in mixtures with fertilizers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seed of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

The preparation and the use of the active compounds according to the invention follow from the examples below.

Preparation Examples

EXAMPLE 1

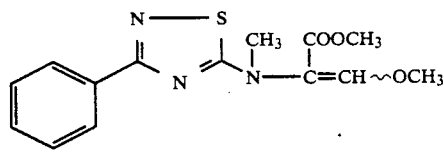

Process (a) - one-pot variant

A mixture of 130.0 g (2.17 mol) of methyl formate and 11.5 g (0.044 mol) of methyl N-(3-phenyl-1,2,4-thiadiazol-5-yl)-N-methyl-2-aminoacetate are added dropwise at 5°–10° C. within the course of 90 minutes to a suspension of 3.3 g (0.11 mol) of an 80% strength sodium hydride suspension in mineral oil. After the initially vigorous reaction has subsided, the mixture is first allowed to come to room temperature and then stirred at 30° C. for 2 hours.

13.9 g (0.11 mol) of dimethyl sulphate are then added to the unisolated methyl N-(3-phenyl-1,2,4-thiadiazol-5-yl)-N-methyl-2-amino-3-hydroxyacrylate and the mixture is stirred at room temperature overnight. For work-up, the mixture is poured onto 2 l of ice water and extracted 3× with diethyl ether, and the organic phase is dried using sodium sulphate. After distilling off the solvent, the crude product is chromatographed on silica gel (eluents, toluene/propanol 10:3).

6.0 g (44% of theory) of methyl N-(3-phenyl-1,2,4-thiadiazol-5-yl)-N-methyl-2-amino-3-methoxyacrylate are obtained.

EXAMPLE 2

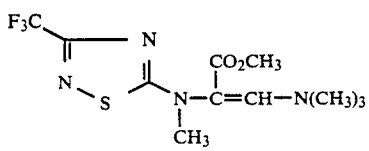

Process (b)

12.8 g (0.05 mol) of N-(3-trifluoromethyl-1,2,4-thiadiazol-5-yl)-N-methyl-glycine methyl ester and 14.7 g (0.10 mol) of dimethylformamide diethyl acetal are heated under reflux for 48 hours. After cooling, the mixture is concentrated under reduced pressure, the residue is stirred with ether and the precipitated crystals are filtered off with suction.

10.0 g (65% of theory) of methyl N-(3-trifluoromethyl-1,2,4-thiadiazol-5-yl)-N-methyl-2-amino-3-N',N'-dimethylamino-acrylate of melting point 130°–131° C. are obtained.

The final products of the formula (I) shown in the following Table 2 are obtained in an analogous manner to the methods described in Examples 1 and 2 and with consideration of the directions in the descriptions for the process according to the invention.

TABLE 2

| Ex. No. | $R^1$ | $R^2$ | $R^3$ | Y | Physical constant |
|---|---|---|---|---|---|
| 3 | phenyl | $CH_3$ | $OCH_3$ | S | $^1$H-NMR*($CDCl_3$, 200 MHz) δ=3.80 (S, 3H), 4.07 (S, 3H), 7.35–7.5(m, 3H) 8.15–8.25(m, 2H) 8.10(s, 1H) |
| 4 | $C(CH_3)_3$ | $CH_3$ | $N(CH_3)_2$ | S | b.p. 173–186° C. 0.5 mbar |
| 5 | n-$C_3H_7$ | $CH_3$ | $N(CH_3)_2$ | S | $^1$H-NMR*($CDCl_3$, 200 MHz)δ=3.2–3.35 (s, 6H) |
| 6 | n-$C_3H_7$ | $C_2H_5$ | $N(CH_3)_2$ | —N(CH_3)— | b.p. 151–155° C. 0.1 mbar |
| 7 | $CCl_2F$ | $C_2H_5$ | $N(CH_3)_2$ | —N(CH_3)— | $^1$H-NMR*($CDCl_3$, 200 MHz) δ=2.9–3.1(s, 6H) |
| 8 | $CCl_2F$ | $C_2H_5$ | $OCH_3$ | —N(CH_3)— | m.p. 89–94° C. |
| 9 | $CCl_2F$ | $CH_3$ | $OCH_3$ | —N(CH_3)— | b.p. 173–178° C. 0.4 mbar |
| 10 | $CClF_2$ | $CH_3$ | $OCH_3$ | —N(CH_3)— | b.p. 147–150° C. 0.2 mbar |
| 11 | $CF_3$ | $CH_3$ | $OCH_3$ | —N(CH_3)— | b.p. 133–137° C. 0.3 mbar |
| 12 | $C(CH_3)_3$ | $CH_3$ | $OCH_3$ | —N(CH_3)— | b.p. 146–151° C. 0.4 mbar |

TABLE 2-continued $$\begin{array}{c} R^1 \\ \diagup \\ N \diagdown_S \end{array} \diagdown Y-C=CH-R^3 \text{ with } COOR^2 \quad (I)$$

| Ex. No. | R¹ | R² | R³ | Y | Physical constant |
|---|---|---|---|---|---|
| 13 | (CH₃)₂CH | CH₃ | OCH₃ | —N(CH₃)— | b.p. 132–141° C. 0.1 mbar |
| 14 | C(CH₃)₃ | CH₃ | OCH₃ | S | b.p. 115–121° C. 0.1 mbar |
| 15 | CCl₃ | CH₃ | OCH₃ | —N(CH₃)— | b.p 114–121° C. 0.7 mbar |
| 16 | C₆H₅—CH₂—S— | CH₃ | OCH₃ | —N(CH₃)— | ¹H-NMR*(CDCl₃, 200 MHz) δ=7.2–7.4 m, (3H) |
| 17 | n-C₃H₇ | CH₃ | OCH₃ | —N(CH₃)— | b.p. 131–134° C. 0.05 mbar |
| 18 | CH₂Cl | CH₃ | OCH₃ | —N(CH₃)— | ¹H-NMR*(CDCl₃, 200 MHz) δ=4.55 s, (2H) |
| 19 | CCl₂F | C₂H₅ | OC₂H₅ | —N(CH₃)— | ¹H-NMR*(CDCl₃, 200 MHz) δ=3.55 s, (3H) |
| 20 | 4-Cl-C₆H₄-CH₂— | CH₃ | —OCH₃ | —N(CH₃)— | ¹H-NMR* δ=3.27s(3H, N—CH₃) 3.73s(3H, CO₂CH₃) 3.93s(3H, COCH₃) |
| 21 | 3,4-Cl₂-C₆H₃-CH₂— | CH₃ | —OCH₃ | —N(CH₃)— | ¹H-NMR* δ=3.38s(3H, N—CH₃) 3.77s(3H, CO₂CH₃) 3.97s(3H, COCH₃) |
| 22 | 4-CH₃O-C₆H₄— | CH₃ | —OCH₃ | —N(CH₃)— | m.p.: 127° C. |
| 23 | 4-CH₃-C₆H₄— | CH₃ | —OCH₃ | —N(CH₃)— | m.p.: 141° C. |
| 24 | 2-F-C₆H₄— | CH₃ | —OCH₃ | —N(CH₃)— | ¹H-NMR* δ=3.27s(3H, N—CH₃) 3.73s(3H, CO₂CH₃) 3.92s(3H, COCH₃) (Z-Isomer) |
| 25 | C₆H₅—CH₂— | CH₃ | —OCH₃ | —N(CH₃)— | ¹H-NMR* δ=3.27s(3H, N—CH₃) 3.72s(3H, CO₂CH₃) 3.91s(3H, OCH₃) (Z-Isomer) |

TABLE 2-continued $$\text{(I)}$$

Structure: R¹-substituted thiadiazole ring connected to C(=N-)-Y-C(COOR²)=CH-R³

| Ex. No. | R¹ | R² | R³ | Y | Physical constant |
|---|---|---|---|---|---|
| 26 | 4-Br-C₆H₄-CH₂- | CH₃ | —OCH₃ | —N(CH₃)— | ¹H-NMR* δ=3.27s(3H, N—CH₃)= 3.73s(34, CO₂CH₃) 3.92s(3H, OCH₃) (Z-Isomer) |
| 27 | ClCH₂— | CH₃ | —OCH₃ | —N(CH₃)— | ¹H-NMR* δ=3.31s(3H, N—CH₃) 3.76s(3H, CO₂CH₃) 3.96s(3H, OCH₃) (Z-Isomer) |
| 28 | 4-F-C₆H₄-CH₂- | CH₃ | —OCH₃ | —N(CH₃)— | ¹H-NMR* δ=3.27s(3H, N—CH₃ 3.73s(3H, CO₂CH₃) 3.92s(3H, OCH₃) (Z-Isomer) |
| 29 | 2,4-Cl₂-C₆H₃-CH₂- | CH₃ | —OCH₃ | —N(CH₃)— | GC/MS:m/e=388 Ret. Index 2689 (Z-Isomers) |
| 30 | 4-O₂N-C₆H₄-CH₂- | CH₃ | —OCH₃ | —N(CH₃)— | GC/MS:m/e=364 Ret. Index 2789 (Z-Isomers) |
| 31 | 2-CF₃-4-Cl-C₆H₃- | CH₃ | —OCH₃ | —N(CH₃)— | ¹H-NMR* δ=3.39s(3H, N—CH₃) 3.78s(3H, CO₂CH₃) 3.98s(3H, OCH₃) (Z-Isomer) |
| 32 | 2,4-Cl₂-C₆H₃-CH₂- | CH₃ | —OCH₃ | —N(CH₃)— | GC/MS:m/e=388 Ret. Index 2737 (E-Isomer) |
| 33 | 4-O₂N-C₆H₄-CH₂- | CH₃ | —OCH₃ | —N(CH₃)— | GC/MS:m/e=364 Ret. Index 2799 (E-Isomer) |
| 34 | 4-F-C₆H₄-CH₂- | CH₃ | —OCH₃ | —N(CH₃)— | ¹H-NMR* δ=3.30s(3H, N—CH₃) 3.75s(3H, CO₂CH₃) 3.97s(3H, OCH₃) (E-Isomer) |
| 35 | ClCH₃— | CH₃ | —OCH₃ | —N(CH₃)— | m.p.: 91–93° C. |
| 36 | C₆H₅-CH=CH— | CH₃ | —OCH₃ | —N(CH₃)— | m.p.: 102–104° C. (Z-Isomer) |
| 37 | 2-pyridyl | CH₃ | —OCH₃ | —N(CH₃)— | ¹H-NMR* δ=3.43s(3H, N—CH₃) 3.76s(3H, CO₂CH₃) 3.96s(3H, OCH₃) (Z-Isomer) |

TABLE 2-continued $$\text{(I)}$$

$$\begin{array}{c} R^1 \\ \Vert \\ N{-}S \end{array} \begin{array}{c} N \\ \Vert \\ \end{array} \begin{array}{c} COOR^2 \\ \vert \\ Y{-}C{=}CH{-}R^3 \end{array}$$

| Ex. No. | R¹ | R² | R³ | Y | Physical constant |
|---|---|---|---|---|---|
| 38 | 3-Cl-phenyl | CH₃ | —OCH₃ | —N(CH₃)— | m.p.: 67° C. |
| 39 | 4-(CH₃)₃C-phenyl-CH₂— | CH₃ | —OCH₃ | —N(CH₃)— | ¹H-NMR* δ=3.27s(3H, N—CH₃) 3.71s(3H, CO₂CH₃) 3.88s(3H, OCH₃) |
| 40 | 4-Cl-phenyl | CH₃ | —OCH₃ | —N(CH₃)— | m.p. 103–106° C. (Z-Isomer) |
| 41 | 4-Br-phenyl | CH₃ | —OCH₃ | —N(CH₃)— | m.p. 90–91° C. (Z-Isomer) |
| 42 | 4-H₃C-phenyl | CH₃ | —OCH₃ | —N(CH₃)— | ¹H-NMR* δ=3.27s(3H, N—CH₃) 3.72s(3H, CO₂CH₃) 3.91s(3H, OCH₃) (Z-Isomer) |
| 43 | 4-CH₃O-phenyl-CH₂— | CH₃ | —OCH₃ | —N(CH₃)— | ¹H-NMR* δ=3.37s(3H, N—CH₃) 3.76s(3H, CO₂CH₃) 3.95s(3H, OCH₃) (Z-Isomer) |
| 44 | 4-(CH₃)₃C-phenyl | CH₃ | —OCH₃ | —N(CH₃)— | ¹H-NMR* δ=3.38s(3H, N—CH₃) 3.75(3H, CO₂CH₃) 3.94s(3H, OCH₃) |
| 45 | phenyl-CH=CH— | CH₃ | —OCH₃ | —N(CH₃)— | GC/MS:m/e=331 Ret. Index 2753 (E-Isomer) |

*The ¹H-NMR spectra were recorded in deuterochloroform (CDCl₃) using tetramethylsilane (TMS) as the internal standard. The chemical shift is indicated as the δ value in ppm.

Preparation of the starting compounds

EXAMPLE (IV-1)

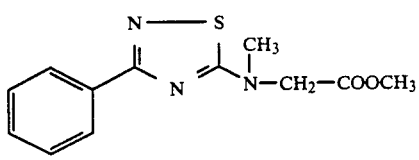

24 g (0.12 mol) of 5-chloro-3-phenyl-1,2,4-thiadiazole, 16.8 g (0.12 mol) of methyl N-methylaminoacetate and 33.2 g (0.24 mol) of ground potassium carbonate are heated overnight in 200 ml of dry 1,4-dioxane. For work-up, the reaction mixture is poured onto ice water and extracted three times with ethyl acetate. After drying over sodium sulphate, 14.2 g (45% of theory) of methyl N-methyl-N-(3-phenyl-1,2,4-thiadiazol-5-yl)-2-aminoscetate of melting point 92° C. are obtained after distilling off the solvent and rerystallizing from ether/ethanol.

The products of the formula (IV) shown in the following Table 3 are obtained in an analogous manner to the method described in Example (IV-1) and with consideration of the directions in the descriptions for the process according to the invention.

TABLE 3

$$\text{(IV)}$$

Structure: R¹ substituted thiadiazole with —Y—CH₂—COOR²

| Ex. | R¹ | R² | Y | Physical Data |
|---|---|---|---|---|
| (IV-2) | phenyl | CH₃ | S | ¹H-NMR* (DMSO-d⁶; 200 MHz) δ=3.72 (s, 3H); 4.38 (s, 2H); 7.54 (mc, 3H); 8 11 (mc, 2H) |
| (IV-3) | phenyl | H | S | m.p. 92° C. |
| (IV-4) | CFCl₂ | C₂H₅ | —N(CH₃)— | ¹H-NMR* (CDCl₃, 200 MHz) δ=3.2 (s, 3H) |
| (IV-5) | CFCl₂ | CH₃ | —N(CH₃)— | ¹H-NMR* (CDCl₃, 200 MHz) δ=3.15 (s, 3H) |
| (IV-6) | CFCl₂ | CH₃ | S | b.p: 129–136° C./0.4 mbar |
| (IV-7) | CFCl₂ | CH₃ | S | b.p: 118–121° C./0.8 mbar |
| (IV-8) | t-C₄H₉ | CH₃ | S | b.p: 88–96° C./0.7 mbar |
| (IV-9) | i-C₃H₇ | CH₃ | S | ¹H-NMR* (CDCl₃, 200 MHz) δ=4.1 (s, 2H) |
| (IV-10) | CF₂Cl | CH₃ | —N(CH₃)— | b.p: 119–124° C. 0.2 mbar |
| (IV-11) | CF₃ | CH₃ | —N(CH₃)— | ¹H-NMR (CDCl₃, 200 MHz) δ=3.2 (s, 3H) |
| (IV-12) | t-C₄H₉ | CH₃ | —N(CH₃)— | b.p.: 108–112° C./0.2 mbar |
| (IV-13) | i-C₃H₇ | CH₃ | —N(CH₃)— | b.p.: 112–118° C./0.2 mbar |
| (IV-17) | phenyl-CH₂S— | CH₃ | —N(CH₃)— | ¹H-NMR (CDCl₃, 200 MHz) δ=3.1 (s, 3H); 4.4 (s, 2H); |
| (IV-14) | C₃H₇ | CH₃ | S | ¹H-NMR (CDCl₃, 200 MHz) δ=4.1 (s, 2H) |
| (IV-15) | C₃H₇ | CH₃ | —N(CH₃)— | ¹H-NMR (CDCl₃, 200 MHz) δ=3.15 (s, 3H) |
| (IV-16) | CHCl₂ | CH₃ | —N(CH₃)— | ¹H-NMR (CDCl₃, 200 MHz) δ=3.15 (s, 3H) |
| (IV-17) | 4-Cl-phenyl | CH₃ | —N(CH₃)— | m.p.: 122° C. |

TABLE 3-continued $$\underset{N\diagdown_S}{\overset{R^1}{\underset{\|}{C}}}\diagup\overset{N}{\underset{C}{\diagdown}}Y-CH_2-COOR^2 \quad (IV)$$

| Ex. | R¹ | R² | Y | Physical Data |
|---|---|---|---|---|
| (IV-18) | 4-Br-C₆H₄- | CH₃ | —N(CH₃)— | Oil |
| (IV-19) | 3-Cl-C₆H₄- | CH₃ | —N(CH₃)— | m.p.: 99° C. |
| (IV-20) | 4-CH₃O-C₆H₄- | CH₃ | —N(CH₃)— | Oil |
| (IV-21) | 4-Cl-C₆H₄-CH₂- | CH₃ | —N(CH₃)— | Oil |
| (IV-22) | 4-biphenylyl | H | —N(CH₃)— | m.p.: 138° C. |
| (IV-23) | 3-CH₃O-4-CH₃-C₆H₃- | CH₃ | —N(CH₃)— | m.p.: 122° C. |
| (IV-24) | 4-biphenylyl | CH₃ | —N(CH₃)— | m.p.: 125° C. |
| (IV-25) | 4-CH₃-C₆H₄- | H | —N(CH₃)— | m.p.: 174° C. |
| (IV-26) | 3,4-Cl₂-C₆H₃- | CH₃ | —N(CH₃)— | m.p.: 123° C. |
| (IV-27) | 4-CH₃-C₆H₄- | CH₃ | —N(CH₃)— | m.p.: 102° C. |
| (IV-28) | 4-Cl-3-CF₃-C₆H₃- | CH₃ | —N(CH₃)— | m.p.: 134° C. |

TABLE 3-continued $$\text{(IV)}$$

Structure (IV): R¹–C(=N–S–N=)–Y–CH₂–COOR²  (1,2,4-thiadiazole with R¹ at 3-position and Y-CH₂-COOR² at 5-position)

| Ex. | R¹ | R² | Y | Physical Data |
|---|---|---|---|---|
| (IV-29) | 4-F-C₆H₄-CH₂- | CH₃ | -N(CH₃)- | m.p.: 76–78° C. |
| (IV-30) | C₆H₅-CH=CH- | CH₃ | -N(CH₃)- | m.p.: 174–177° C. |
| (IV-31) | ClH₂C- | CH₃ | -N(CH₃)- | m.p.: 60–62° C. |
| (IV-32) | 2-F-C₆H₄-CH₂- | CH₃ | -N(CH₃)- | m.p.: 74–76° C. |
| (IV-33) | 2,4-Cl₂-C₆H₃-CH₂- | CH₃ | -N(CH₃)- | m.p.: 53–55° C. |
| (IV-34) | C₆H₅-CH₂- | CH₃ | -N(CH₃)- | m.p.: 56–55° C. |
| (IV-35) | 4-Br-C₆H₄-CH₂- | CH₃ | -N(CH₃)- | m.p.: 78–81° C. |
| (IV-36) | 4-O₂N-C₆H₄-CH₂- | CH₃ | -N(CH₃)- | m.p.: 76° C. |
| (IV-37) | C₆H₅-CH=CH- | CH₃ | -N(CH₃)- | m.p.: 109–110° C. |
| (IV-38) | 2-pyridyl- | CH₃ | -N(CH₃)- | m.p.: 101–102° C. |
| (IV-39) | 4-(CH₃)₃C-C₆H₄-CH₂- | CH₃ | -N(CH₃)- | Oil |
| (IV-40) | 3-Cl-C₆H₄-CH₂- | CH₃ | -N(CH₃)- | Oil |

TABLE 3-continued $$\begin{array}{c} R^1 \\ \diagdown \\ N \diagup^N \diagdown_S \diagdown Y-CH_2-COOR^2 \end{array} \quad (IV)$$

| Ex. | R¹ | R² | Y | Physical Data |
|---|---|---|---|---|
| (IV-41) | CH₃—⟨C₆H₄⟩—CH₂— | CH₃ | —N(CH₃)— | m.p.: 81° C. |
| (IV-42) | CH₃O—⟨C₆H₄⟩—CH₂— | CH₃ | —N(CH₃)— | m.p.: 51–52° C. |
| (IV-43) | Cl,CF₃-disubstituted—⟨C₆H₃⟩—CH₂— | CH₃ | —N(CH₃)— | m.p.: 80° C. |
| (IV-44) | (CH₃)₃C—⟨C₆H₄⟩— | CH₃ | —N(CH₃)— | m.p.: 114° C. |

*The ¹H-NMR NMR spectra were recorded in deuterated dimethylsulphoxide (d₆DMSO) or in dueteriochloroform (CDCl₃) using tetramethylsilane (TMS) as the internal standard. The chemical shift is indicated as the δ value in ppm.

Use Examples

In the following use examples, the compound shown below was employed as a comparison substance:

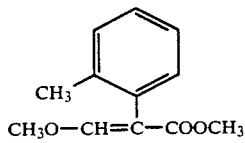

(A)

Methyl 3-methoxy-2-(2-methylphenyl)-acrylate (known from EP 178,826).

EXAMPLE A

Pyricularia test (rice)/protective
Solvent: 12.5 parts by weight of acetone
Emulsifier: 0.3 part by weight of alkylaryl polyglycol ether To produce a suitable preparation of active compound, 1 part by weight of active compound is mixed with the stated amount of solvent, and the concentrate is diluted with water and the stated amount of emulsifier to the desired concentration.

To test for protective activity, young rice plants are sprayed with the preparation of active compound until dripping wet. After the spray coating has dried off, the plants are inoculated with an aqueous spore suspension of Pyridularia oryzae. The plants are then placed in a greenhouse at 100% relative atmospheric humidity and 25° C.

Evaluation of the disease infestation is carried out 4 days after the inoculation.

In this test, for example, the compound according to preparation Example 1 shows a clearly superior activity compared to the prior art.

EXAMPLE B

Leptosphaeria nodorum test (wheat)/protective
Solvent: 100 parts by weight of dimethylformamide
Emulsifier: 0.25 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a spore suspension of Leptosphaeria nodorum. The plants remain for 48 hours in an incubation cabin at 20° C. and 100% relative atmospheric humidity.

The plants are placed in a greenhouse at a temperature of about 15° C. and a relative atmospheric humidity of about 80%.

Evaluation is carried out 10 days after the inoculation.

In this test, for example, the compound according to Preparation Example 1 shows a clearly superior activity compared to the prior art.

It is understood that the specification and examples are illustrative but not limitative of the present invention and that other embodiments within the spirit and scope of the invention will suggest themselves to those skilled in the art.

We claim:

1. A thiadiazole-substituted acrylic acid ester of the formula

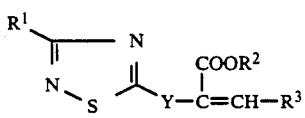

in which
- R¹ represents hydrogen, methyl, ethyl, n- or i-propyl, n-, i-, s- or t-butyl, straight-chain or branched alkyl having 1 to 4 carbon atoms, which is monosubstituted to hexasubstituted by identical or different substituents from the group consisting of fluorine and chlorine, or straight-chain or branched alkyl having 1 to 4 carbon atoms which is substituted by phenylthio or phenyloxy which in each case are unsubstituted or monosubstituted to trisubstituted by identical or different substituents, the phenyl substituents being the substituents mentioned below in the definition of R¹ or;
- R¹ represents allyl, n- or i-butenyl, or benzyl, phenylethyl, phenylethenyl, phenyl, naphthyl, pyridyl, thienyl or furyl in each case optionally monosubstituted to trisubstituted in the aryl moiety or in the heteroaryl moiety by identical or different substituents selected from the group consisting of fluorine, chlorine, bromine, cyano, nitro, methyl, ethyl, n- or i-propyl, n-, i-, s- or t-butyl, methoxy, ethoxy, n- or i-propoxy, methylthio, trifluoromethyl, trifluoromethoxy, difluoromethoxy, trifluoromethylthio, methoxycarbonyl, ethoxycarbonyl, methoximinomethyl, ethoximinomethyl, methoximinoethyl, ethoximinoethyl, cyclopentyl, cyclohexyl, 1,3-propanediyl, but-2-ene-di-1,4-yl, 1,4-butanediyl, and phenyl, benzyl, phenoxy or benzyloxy in each case unsubstituted or monosubstituted to trisubstituted in the phenyl moiety by identical or different substituents from the group consisting of fluorine, chlorine, bromine, methyl, ethyl, methoxy, ethoxy, methylthio, trifluoromethyl, difluoromethoxy, trifluoromethoxy and trifluoromethylthio,
- R² represents methyl, ethyl, n- or i-propyl, n-, i-, s- or t-butyl,
- R³ represents dialkylamino each having 1 to 4 carbon atoms in the individual straight-chain or branched, identical or different alkyl moieties or a radical —Z—R⁴,
- Y represents oxygen, sulphur or a radical

- R⁴ represents methyl, ethyl, n- or i-propyl, n-, i-, s- or t-butyl or benzyl which is unsubstituted or monosubstituted to trisubstituted by identical or different substituents as those mentioned for R¹;
- R⁵ represents hydrogen, methyl, ethyl, n- or i-propyl, n-, i-, s- or t-butyl and
- Z represents oxygen or sulphur.

2. A thiadiazole-substituted acrylic acid ester according to claim 1, in which
- R¹ represents hydrogen, methyl, ethyl, n- or i-propyl, t-butyl, alkyl having 1 or 2 carbon atoms, which is monosubstituted to pentasubstituted by identical or different substituents from the group consisting of fluorine and chlorine or alkyl having 1 or 2 carbon atoms, which is substituted by phenylthio and phenyloxy which are in each case unsubstituted or monosubstituted or disubstituted by identical or different substituents, the phenyl substituents being those mentioned below in the definition of R¹; or
- R¹ represents phenyl or naphthyl in each case optionally monosubstituted to trisubstituted by identical or different substituents, selected from the group consisting of fluorine, chlorine, bromine, cyano, nitro, methyl, ethyl, n- or i-propyl, n-, i-, s- or t-butyl, methoxy, ethoxy, n- or i-propoxy, methylthio, trifluoromethyl, trifluoromethoxy, difluoromethoxy, trifluoromethylthio, methoxycarbonyl, ethoxycarbonyl, methoximinomethyl, ethoximinomethyl, methoximinoethyl, ethoximinoethyl, cyclopentyl, cyclohexyl, 1,3-propanediyl, 1,4-butanediyl and phenyl, phenoxy, benzyl or benzyloxy disubstituted by identical or different substituents from the group consisting of fluorine, chlorine, bromine, methyl and ethyl,
- R² represents methyl or ethyl,
- R³ represents dimethylamino, diethylamino or a radical —Z—R⁴
- Y represents oxygen, sulphur or a radical

- R⁴ represents methyl, ethyl, n- or i-propyl or benzyl,
- R⁵ represents hydrogen, methyl or ethyl and
- Z represents oxygen or sulphur.

3. A thiadiazole-substituted acrylic acid ester according to claim 1, in which
- R¹ represents hydrogen, methyl, ethyl, n- or i-propyl, t-butyl, methyl which is monosubstituted to trisubstituted by identical or different substituents from the group consisting of fluorine, chlorine and phenyl, phenyloxymethyl or phenylthiomethyl which are in each case optionally monosubstituted or disubstituted by identical or different substituents, selected from the group consisting of fluorine, chlorine, bromine, cyano, nitro, methyl, ethyl, methoxy, ethoxy, methylthio, trifluoromethyl, trifluoromethyl, trifluoromethylthio, methoxycarbonyl, ethoxycarbonyl, methoximinomethyl, cyclopentyl, 1,3-propanediyl, methoximinoethyl and phenyl, phenoxy, benzyl or benzyloxy which are optionally monosubstituted or disubstituted by identical or different substituents from the group consisting of fluorine, chlorine, bromine and methyl,
- R² represents methyl or ethyl,
- R³ represents methoxy, ethoxy, methylthio or dimethylamino and
- Y represents an N-methyl radical or sulphur.

4. A compound according to claim 1, wherein such compound is methyl N-(3-phenyl-1,2,4-thiadiazol-5-yl)-N-methyl-2-amino-3-methoxyacrylate of the formula

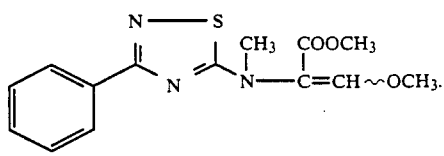

5. A compound according to claim 1, wherein such compound is ethyl N-(3-dichlorofluoromethyl-1,2,4-thiadiazol-5-yl)-N-methyl-2-amino-3-methoxyacrylate of the formula

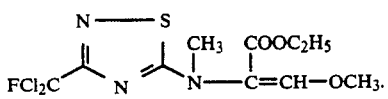

6. A compound according to claim 1, wherein such compound is methyl N-(3-dichlorofluoromethyl-1,2,4-thiadiazol-5-yl)-N-methyl-2-amino-3-methoxyacrylate of the formula

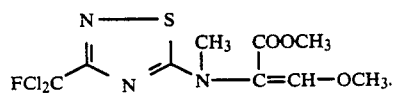

7. A compound according to claim 1, wherein such compound is methyl N-(3-benzylthio-1,2,4-thiadiazol-5-yl)-N-methyl-2-amino-3-methoxyacrylate of the formula

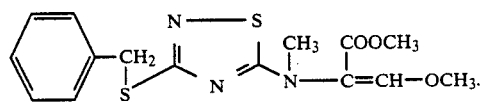

8. A compound according to claim 1, wherein such compound is methyl N-(3-chloromethyl-1,2,4-thiadiazol-5-yl)-N-methyl-2-amino-3-methoxyacrylate of the formula

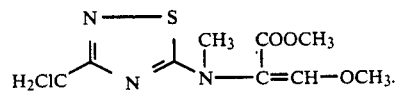

9. A compound according to claim 1, wherein such methyl-N-(3-p-chlorophenyl-1,2,4-thiadiazol-5-yl)-N-methyl-2-amino-3-methoxyacrylate of the formula

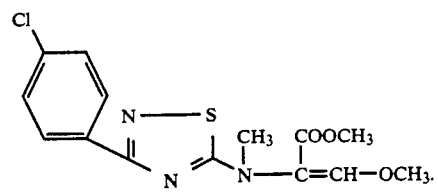

10. A compound according to claim 1, wherein such compound is methyl N-(3-p-bromophenyl-1,2,4-thiadiazol-5-yl)-N-methyl-2-amino-3-methoxyacrylate of the formula

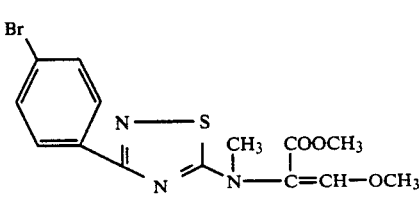

11. A fungicidal composition comprising a fungicidally effective amount of a compound according to claim 1 and a diluent.

12. A method of combating fungi which comprises applying to such fungi or to a fungus habitat a fungicidally effective amount of a compound according to claim 1.

13. The method according to claim 12, wherein such compound is
   methyl N-(3-phenyl-1,2,4-thiadiazol-5-yl)-N-methyl-2-amino-3-methoxyacrylate,
   ethyl N-(3-dichlorofluoromethyl-1,2,4-thiadiazol-5-yl)-N-methyl-2-amino-3-methoxyacrylate,
   methyl N-(3-dichlorofluoromethyl-1,2,4-thiadiazol-5-yl)-N-methyl-2-amino-3-methoxyacrylate,
   methyl N-(3-benzylthio-1,2,4-thiadiazol-5-yl)-N-methyl-2-amino-3-methoxyacrylate,
   methyl N-(3-chloromethyl-1,2,4-thiadiazol-5-yl)-N-methyl-2-amino-3-methoxyacrylate;
   methyl-N-(3-p-chlorophenyl-1,2,4-thiadiazol-5-yl)-N-methyl-2-amino-3-methoxyacrylate, or
   methyl N-(3-p-bromophenyl-1,2,4-thiadiazol-5-yl)-N-methyl-2-amino-3-methoxyacrylate.

* * * * *

UNITED STATES PATENT AND TRADEMARK OFFICE
CERTIFICATE OF CORRECTION

PATENT NO. : 5,036,085

DATED : July 30, 1991

INVENTOR(S) : Heinemann et al.

It is certified that error appears in the above-identified patent and that said Letters Patent is hereby corrected as shown below:

Col. 36, line 20   After " benzyloxy " insert -- in each case optionally monosubstituted or --

Col. 37, line 45   Before " methyl-N- " insert -- compound is --

Signed and Sealed this

Thirteenth Day of April, 1993

*Attest:*

STEPHEN G. KUNIN

*Attesting Officer*   *Acting Commissioner of Patents and Trademarks*